(12) United States Patent
Steyn et al.

(10) Patent No.: US 9,014,409 B2
(45) Date of Patent: Apr. 21, 2015

(54) BATTERY DOOR

(71) Applicant: Phitek Systems Limited, Newmarket (NZ)

(72) Inventors: Andre Steyn, Auckland (NZ); Aran Pudney, Auckland (NZ)

( * ) Notice: Subject to any disclaimer, the term of this patent is extended or adjusted under 35 U.S.C. 154(b) by 0 days.

(21) Appl. No.: 13/932,502

(22) Filed: Jul. 1, 2013

(65) Prior Publication Data

US 2013/0294633 A1 Nov. 7, 2013

Related U.S. Application Data

(63) Continuation of application No. 11/900,498, filed on Sep. 12, 2007, now abandoned.

(30) Foreign Application Priority Data

Sep. 14, 2006 (NZ) ........................................ 549912

(51) Int. Cl.
*H04R 1/10* (2006.01)
*H04R 5/033* (2006.01)

(52) U.S. Cl.
CPC ............ *H04R 1/1091* (2013.01); *H04R 1/1008* (2013.01); *H04R 1/1025* (2013.01); *H04R 1/1066* (2013.01); *H04R 1/1083* (2013.01); *H04R 5/033* (2013.01); *H04R 2420/07* (2013.01)

(58) Field of Classification Search
CPC ...... H04R 5/033; H04R 5/0335; H04R 25/60; H04R 25/602; H04R 25/65; H04R 2201/10; H04R 1/10; H04R 1/1008; H04R 1/1091; H04R 1/025; H04R 1/033; H04R 1/1075

USPC ......... 381/370, 371, 372, 374, 384, 322, 323, 381/324, 386, 395, 373, 189, 394; 379/430
See application file for complete search history.

(56) References Cited

U.S. PATENT DOCUMENTS

| | | | | |
|---|---|---|---|---|
| 3,306,991 | A * | 2/1967 | Wood | 381/72 |
| 4,937,606 | A * | 6/1990 | Soumi et al. | 396/539 |
| 5,293,647 | A * | 3/1994 | Mirmilshteyn et al. | 2/209 |
| 5,519,783 | A * | 5/1996 | Kumar | 381/370 |
| 5,604,813 | A * | 2/1997 | Evans et al. | 381/71.6 |
| 6,252,970 | B1 * | 6/2001 | Poon et al. | 381/374 |
| 6,385,325 | B1 * | 5/2002 | Nageno et al. | 381/374 |
| 6,522,613 | B1 * | 2/2003 | Frankeny et al. | 720/655 |
| 6,829,365 | B1 * | 12/2004 | Kim | 381/370 |

(Continued)

FOREIGN PATENT DOCUMENTS

| | | |
|---|---|---|
| DE | 202004017589 | 4/2005 |
| EP | 1641314 | 3/2006 |
| JP | 200753059 | 3/2007 |

*Primary Examiner* — Curtis Kuntz
*Assistant Examiner* — Joshua A Kaufman

(57) ABSTRACT

An earcup assembly for a headset may include a housing having a first side adapted to engage the head of a user when in use and a second side opposite thereto. A recess provided in the second side of the housing receives and stores a battery. A battery door is arranged to slidably engage the second side of the housing such that the battery door may be moved between a first, open position in which the recess is accessible to a user and a second, closed position in which the recess is covered by the battery door. Preferably, the earcup assembly includes active noise reduction circuitry. One or a pair of such earcup assemblies may be arranged to form a headset, wherein the assemblies are coupled to a headband via yokes.

20 Claims, 6 Drawing Sheets

(56) References Cited

U.S. PATENT DOCUMENTS

| | | | |
|---|---|---|---|
| 6,850,288 B2* | 2/2005 | Kurokawa | 348/836 |
| 7,068,242 B2* | 6/2006 | Kiyokawa | 345/8 |
| 7,245,737 B2* | 7/2007 | Amae et al. | 381/374 |
| 7,406,172 B2* | 7/2008 | Amae | 379/430 |
| 7,412,070 B2* | 8/2008 | Kleinschmidt et al. | 381/374 |
| 8,761,428 B2* | 6/2014 | Amae | 381/378 |
| 2004/0190743 A1* | 9/2004 | Chen | 381/370 |
| 2005/0105755 A1* | 5/2005 | Yueh | 381/371 |
| 2005/0213774 A1* | 9/2005 | Kleinschmidt et al. | 381/71.6 |
| 2007/0223720 A1* | 9/2007 | Goldberg et al. | 381/74 |
| 2008/0069391 A1* | 3/2008 | Steyn et al. | 381/371 |
| 2009/0041275 A1* | 2/2009 | Crook | 381/323 |
| 2009/0268935 A1* | 10/2009 | Dillinger | 381/371 |
| 2010/0310093 A1* | 12/2010 | Semcken | 381/104 |
| 2011/0142249 A1* | 6/2011 | Shinozaki | 381/71.6 |
| 2012/0328143 A1* | 12/2012 | Ohtani et al. | 381/384 |
| 2013/0343591 A1* | 12/2013 | Brunner et al. | 381/371 |
| 2014/0086429 A1* | 3/2014 | Semcken | 381/74 |

* cited by examiner

BATTERY DOOR

This continuation application claims priority to and the benefit of U.S. patent application Ser. No. 11/900,498, filed Sep. 12, 2007.

FIELD OF THE INVENTION

The present invention relates to an earcup assembly for a headset and a headset incorporating such an assembly. More particularly, the invention relates to a battery door for an earcup assembly. The invention may be applied to both ear muffs or hearing protectors and headphones, especially to those provided with active noise reduction functionality.

BACKGROUND

Active noise reduction has been developed for use in ear muffs and headphones. Active noise reduction involves sensing background noise and playing a copy of the background noise substantially simultaneously to the original background noise. The copy of the noise is rotated to be 180° out of phase with respect to the original background noise so that, when combined, the two signals destructively interfere. Ideally, the two signals cancel each other out. Incorporation of active noise reduction in headsets requires the addition of a power supply, which must be built in, or electrically coupled to, the headset. To maintain the portable nature of headsets, some prior art arrangements have included a battery compartment in an earcup of the headset.

United States patent application Publication No. 2005/0213774 discloses one such arrangement for a noise reducing headset. The headset has a pair of earcups, each earcup being attached to a corresponding yoke assembly. One of the earcups is provided with a battery door that may be opened to allow insertion and removal of a battery from a recess in the earcup. To prevent a battery from inadvertently falling from the recess in the earcup, the battery door is positioned so as to be covered by the yoke assembly when the headset is worn by a user, thereby blocking the battery door from opening. Whilst headsets configured according to the aforementioned publication may perform the generally desired function of active noise reduction, they are not without shortfalls. For example, the yoke may obstruct access to the battery door and/or obstruct access to the battery compartment after the battery door has been opened, thereby making it awkward for a user to replace a battery. Additionally, users must remove such headsets and place them in a particular configuration to be able to access the battery, which may be difficult in particular environments where it is not possible to place the headset down, for example, on a table. Also, where the battery door is not properly closed by a user, movement of the earcup in the yoke may be restricted and may ultimately lead to damaging of the door and/or the yoke.

SUMMARY OF THE INVENTION

It is an object of the invention to provide an improved earcup assembly for a headset, preferably an active noise reducing headset.

Alternatively, is an object of the invention to provide an improved headset, preferably an improved active noise reducing headset.

Alternatively, it is an object to at least provide the public with a useful choice.

According to a first aspect of the invention, there is provided an earcup assembly for a headset. The earcup assembly comprises a housing having a first side adapted to engage the head of a user when in use and a second side opposite thereto. A recess is provided in the second side of the housing for receiving and storing a battery. A battery door is also provided, together with means for slidably engaging the battery door with the second side of the housing. The means for slidably engaging is adapted to enable positioning of the battery door in a first, open position in which the recess is accessible to a user and a second, closed position in which the recess is covered by the battery door.

Preferably, the earcup assembly includes means for actively reducing background noise.

Preferably, the earcup assembly includes means for selectively retaining the battery door in the second, closed position to prevent unintentional escape of a battery from the recess.

Additionally or alternatively, means may be provided for selectively retaining the battery door in the first, open position to provide for easier removal and insertion of batteries into the recess.

Preferably, the first side of the housing is substantially planar and the means for slidably engaging the battery door is adapted to slide the battery door in a plane substantially parallel to the first side of the housing.

Preferably, the means for slidably engaging the battery door is adapted to rotatably slide the battery door across the surface of the second side of the housing.

Additionally or alternatively, the means for slidably engaging the battery door may be adapted to linearly slide the battery door across the surface of the second side of the housing.

Preferably, the battery door is adapted to cover substantially the entire second side of the housing when in the second, closed position, but may alternatively be dimensioned to cover only a portion of the second side of the housing, said portion including at least a portion of the recess. As a further alternative, the battery door may be proportioned to protrude over one or more edges of the second side of the housing when in the closed position. Such embodiments may enable a user to more easily initiate sliding of the battery door over the surface of the second side of the housing.

Preferably, the earcup assembly includes a loud speaker located inside the housing.

According to a second aspect, there is provided a headset including a first earcup assembly, the first earcup assembly being in accordance with an earcup assembly of the first aspect.

Preferably, the headset includes a headband coupled to a first yoke assembly and means for coupling the first earcup assembly to the first yoke assembly.

Preferably, the headset includes a second earcup assembly, a second yoke assembly coupled to the headband and means for coupling the second earcup assembly to the second yoke assembly. The second earcup assembly may be configured in accordance with the first aspect of the invention. Alternatively, the second earcup assembly may omit one or more features of the first earcup assembly. In particular, a recess for a battery and or a battery door may be omitted from the second earcup assembly. In this case, where power is required to be supplied to both earcup assemblies (such as in most applications of active noise reduction), means are preferably provided for electrically coupling circuitry in the first earcup assembly to circuitry in the second earcup assembly. This electrical coupling may be effected by way of a conductor provided or formed in the headband of the headset.

The positioning of the battery door on the second side of the housing, away from the yoke, may help to reduce obstruction of the door by the yoke and also the likelihood of damage being caused to the door by the yoke (or vice versa) when the battery door is open, particularly in embodiments in which means are provided to limit the extent of rotation of an earcup assembly in a respective yoke assembly. This arrangement of the battery door may also enable access by a user to the recess via the battery door when the headset is being worn. Such embodiments may enable a user to more easily change batteries because it is not necessary to hold the headset at the same time as performing the other functions of opening the battery door and holding the batteries.

Further aspects of the invention, which should be considered in all its novel aspects, will become apparent to those skilled in the art upon reading the following description which provides at least one example of a practical application of the invention.

BRIEF DESCRIPTION OF THE DRAWINGS

One or more embodiments of the invention will be described below by way of example only and without intending to be limiting with reference to the following drawings, in which.

DETAILED DESCRIPTION OF PREFERRED EMBODIMENTS

Figure 1:
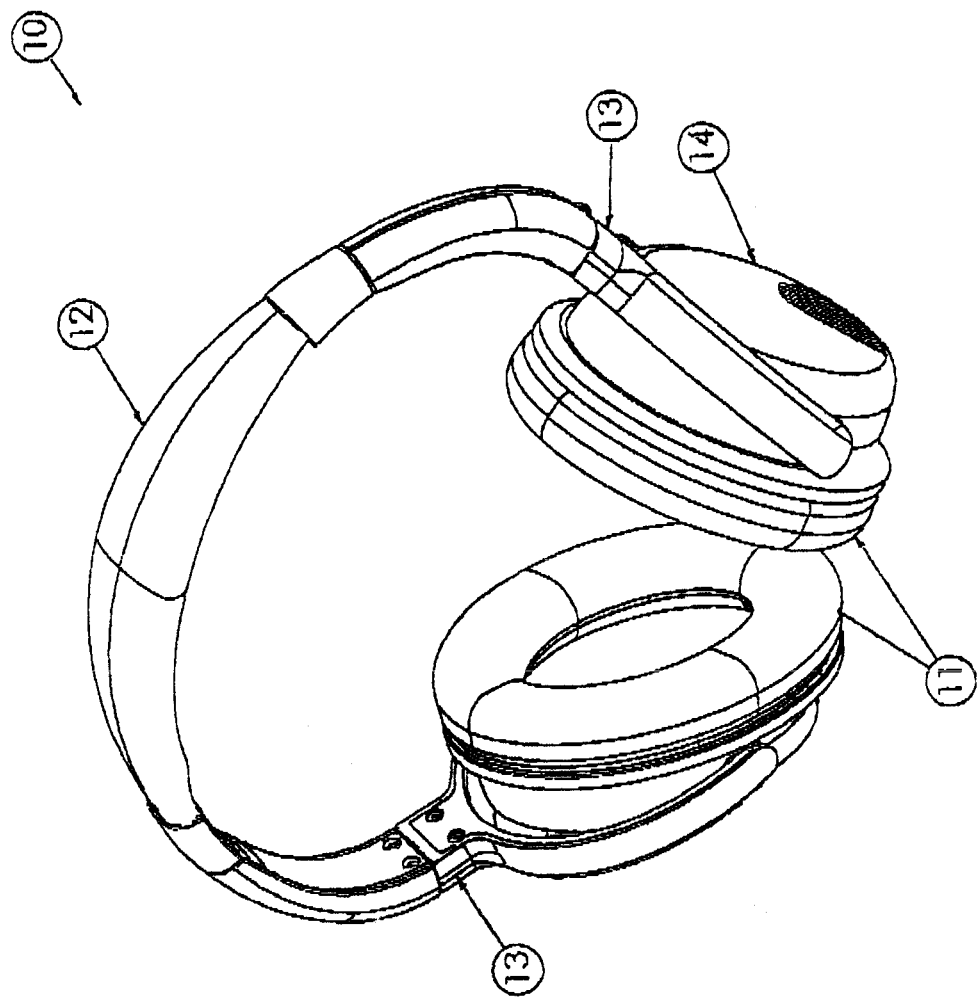
FIG. 1 is a perspective view of a headset.

Referring to FIG. 1, a headset is shown generally referenced 10 and including earcups 11 linked by headband 12 via yokes 13. Alternative configurations of headsets will be known to one of skill in the art and the present invention is not intended to be limited to the particular configuration shown. The invention may be readily applied to alternative headset configurations without invention, including those in which only a single earcup is utilised. Moreover, headsets are defined as including both headphones and ear protectors or muffs and the term is not to be unduly limited. In the case of headphones, the earcup 11 or earcups 11 may include speakers for providing sound, such as music, to a user and may be coupled to a signal source via appropriate, known wired or wireless technology.

One or both of the earcups 11 may be provided with circuitry (not shown) for active noise reduction. Those skilled in the art would readily be able to select and configure circuitry for performing active noise reduction and only details of the circuitry that impact on the present invention are included herein to avoid ambiguity as to the scope of the invention. Active noise reduction circuitry senses background noise (i.e., noise external to the earcups when the headset is worn by a user) and generates a 180° phase shifted replica thereof. The replica of the background noise has an amplitude substantially the same as or proportional to the original background noise but its polarity is reversed. By generating the replica substantially concurrently to the original background noise, the two waveforms destructively interfere, thereby reducing the effects of background noise on the user.

Active noise reduction circuitry requires a power source to operate. According to embodiments of the present invention, one or both of the earcups 11 may be provided with a battery compartment 21 (see FIGS. 2a and 2b) that is covered by a battery door 14. The battery door 14 allows access to the battery compartment 21 at times when batteries need to be inserted or removed. At other times, the battery door 14 may be closed to protect the battery 22 (see FIGS. 2a and 2b) and any internal circuitry accessible via the battery compartment 21. In particular embodiments, the battery door 14 may be used to effect electrical connection.

If only one of the earcups 11 is provided with a battery compartment 21 (which is beneficial in reducing the overall weight of the headset), electrical coupling means (not shown) may be provided between the earcups 11. The electrical coupling means may be provided, at least in part, by a suitable conductor formed in or attached to the headband 12.

The present invention is not limited to the inclusion of a battery door for an earcup having active noise reduction circuitry. The skilled man will be aware of other situations in which a power supply is required in a headset and it is intended these be covered by the present invention. For example, the invention may be applied to wireless headsets that do not include active noise reduction circuitry.

FIGS. 2a, 2b, 3a and 3b illustrate one of the earcups 11 of FIG. 1 in greater detail. It should be noted that only one of the earcups of FIG. 1 may be provided with a battery compartment. In such embodiments where the headset includes two earcups, the earcups are preferably electrically coupled if power is required in both earcups, such as in the application of active noise reduction for most situations.

Figure 2A:
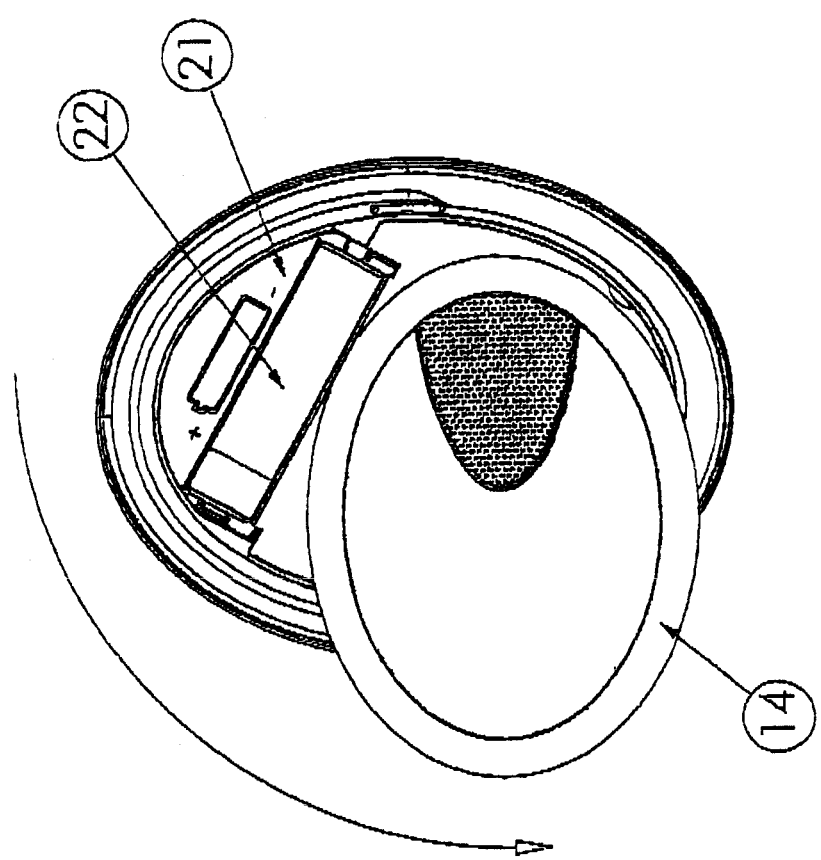
FIGS. 2a and 2b are views of one earcup of the headset of FIG. 1, in more detail, in a first configuration.
Figure 3A:
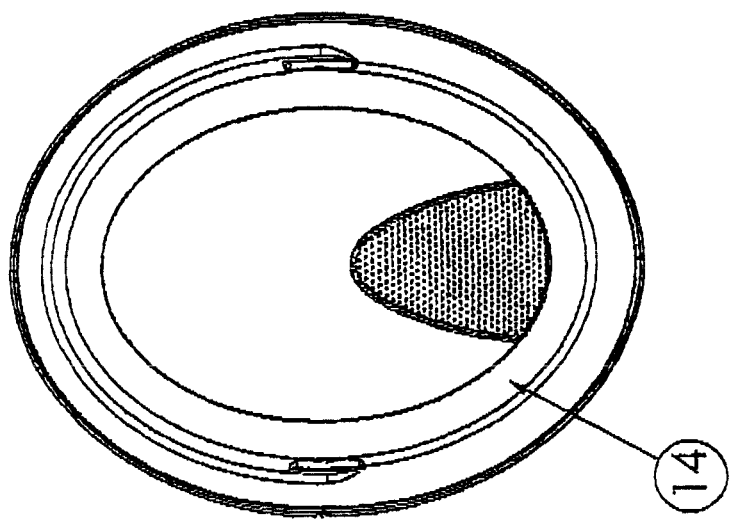
FIGS. 3a and 3b are corresponding views of the earcup of FIGS. 2a and 2b in a second configuration.
Figure 2B:
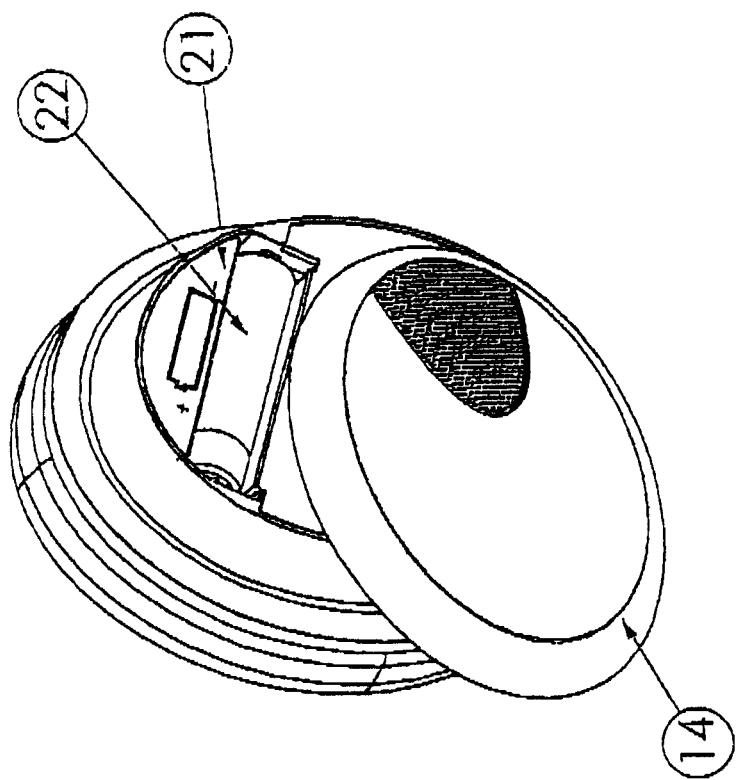
Figure 3B:
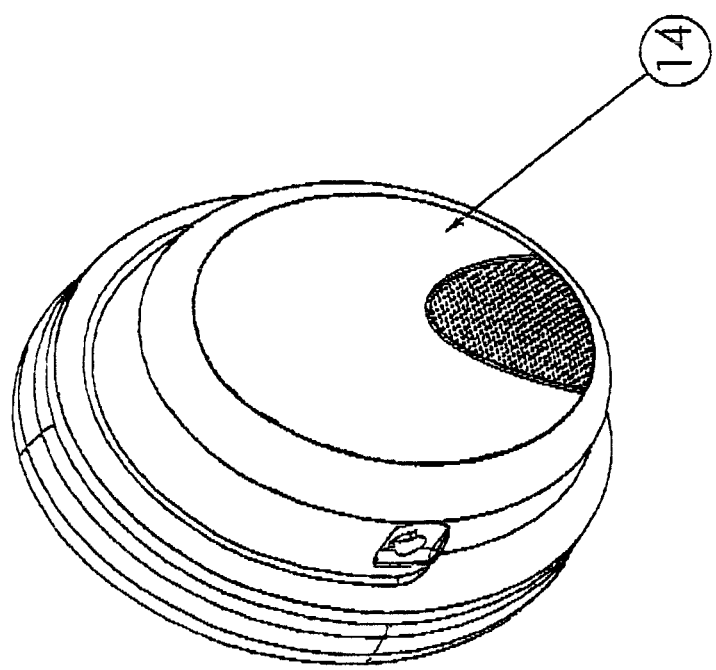

FIGS. 2a and 2b show the battery door 14 in a first, open position in which the battery compartment 21 may be accessed to allow for removal and/or insertion of a battery 22. FIGS. 3a and 3b show the battery door 14 in a second, closed position in which access to the battery compartment 21 is blocked. The battery door 14 is moveable between the two positions by rotatably sliding the battery door 14 through an arc over an outer surface of the housing of the earcup 11. In alternative embodiments, the battery door 14 may be arranged to slide in a substantially straight line across the outer surface of the housing. The invention also covers embodiments in which a combination of linear and rotational movement is used to transition the battery door 14 between first and second positions.

The earcup 11 is configured with a first surface adapted to engage the head of a user when in use. For comfort, and to provide an acoustic seal of some measure between the earcup 11 and the user's head, padding may be provided around the edge of the first surface. In some embodiments, the earcup 11 houses a loud speaker that is used, for example, to play music to a user. In alternative embodiments, the earcup 11 may house passive noise reduction means, where the earcup 11 is used for ear protection. Instead of or in addition to the loud speaker or the passive noise reduction means, the earcup 11 may house active noise reduction circuitry.

The earcup 11 has a second, outer surface, opposite to the first surface, that may be substantially planar, domed or of some other configuration dependent on the desired appearance. The battery door 14 may form at least a portion of the second, outer surface. Preferably, the entire second, outer surface is formed by the battery door 14.

The means for slidably engaging is preferably arranged so that the battery door 14 may be moved in a plane substantially parallel to the first surface of the earcup 11. In such embodiments, through particular design of the means for slidably engaging (e.g. allowing for linear sliding movement of the door downwards when the headset is worn, away from the portion of the yoke coupled to the headband) and/or by provision of means (such as a mechanical stop) for limiting the extent of rotation of the earcup 11 in the yoke 13, the battery door 14 may be opened when the headset 10 is worn without any impingement on the motion of the battery door 14 caused by other portions of the headset. Furthermore, such a configuration results in a minimal risk of a portion of the user being hit by or impinging on movement of the door as it is opened when the headset 10 is worn.

Figure 3C:
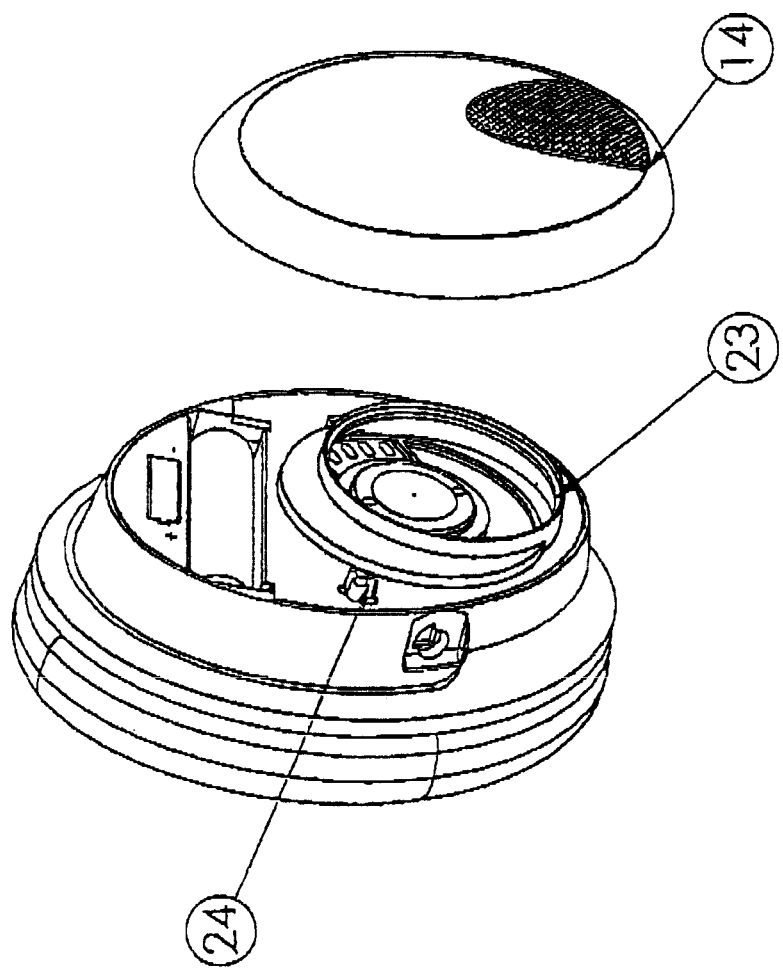
FIGS. 3c and 3D are exploded views of the earcup of FIGS. 2a, 2b, 3a and 3b showing an embodiment of the means for slidably engaging the battery door with the earcup.
Figure 3D:
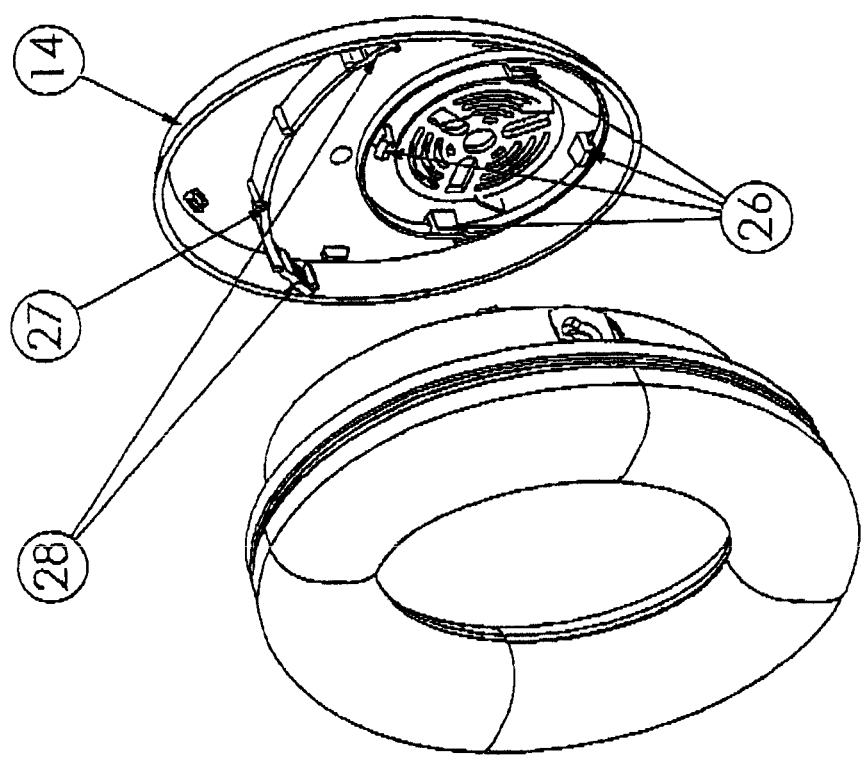

FIGS. 3c and 3d are exploded views of the earcup 11 showing a preferred arrangement of the means for slidably engaging. Referring to FIG. 3c, earcup 11 includes a circular snap ring 23 and detent spring 24. Referring to FIG. 3d, battery door 14 includes snaps 26, rail 27 and detent pockets 28.

To assemble the earcup 11, the battery door 14 is pushed into contact with the earcup 11 so that the snaps 26 engage the circular snap ring 23 by means of a snap fit. The particular configuration shown in FIGS. 3c and 3d provides for rotational sliding movement. It would be readily apparent as to how this arrangement may be adapted to provide linear sliding movement. Furthermore, the invention is not limited to the type of configuration shown, which is merely by way of example, and may be readily adapted to arrive at alternative manners in which to couple the battery door 14 to the earcup 11 whilst allowing for sliding movement as would be apparent to one skilled in the art.

When the battery door 14 is rotated between the first and second positions, detent spring 24 slides along the inside of rail 27. When the door 14 is either fully open or closed, the detent spring engages one or other of the detent pockets 28, thereby locking the door 14 in place. Locking the door 14 in the open position can assist a user in replacing a battery by avoiding the need to hold the door 14 open as the battery is removed/inserted. Rail 27 may further serve to ensure that the battery 22 is held firmly in the battery compartment 21 when the door 14 is in the closed position.

The invention departs from previous designs of headsets requiring a battery to be stored in one or both earcups by providing easy access to the battery compartment and without attempting to hide the battery compartment behind the yoke.

Application of the invention is not limited to headsets and the inventive aspects of the battery door configuration may be applied to other articles, such as a remote control, without inventive activity. It should further be noted that various changes and modifications to the presently preferred embodiments described herein will be apparent to those skilled in the art. Such changes and modifications may be made without departing from the spirit and scope of the present invention and without diminishing its attendant advantages. It is therefore, intended that such changes and modifications be included within the present invention.

The invention claimed is:

1. An earcup assembly for a headset, the earcup assembly comprising:
   a housing having a first side adapted to engage the head of a user when in use and a second side opposite thereto;
   a yoke assembly pivotally coupled to the housing;
   a recess in the second side of the housing for receiving and storing a battery; and
   a battery door;
   wherein the housing and the battery door are pivotally coupled such that the battery door is moveable in a plane parallel to the housing between a first, open position in which the recess is accessible to a user and a second, closed position in which the recess is covered by the battery door, and wherein the battery door is moveable to the open position without obstruction by the yoke when the headset is being worn by the user.

2. The earcup assembly of claim 1, further comprising means for actively reducing background noise.

3. The earcup assembly of claim 1, further comprising means for selectively retaining the battery door in the second, closed position.

4. The earcup assembly of claim 1, further comprising means for selectively retaining the battery door in the first, open position.

5. The earcup assembly of claim 1, wherein the first side of the housing is substantially planar, and the earcup assembly further comprises a means for slidably engaging the battery door, which is adapted to slide the battery door in a plane substantially parallel to the first side of the housing.

6. The earcup assembly of claim 5, wherein the means for slidably engaging the battery door is adapted to rotatably slide the battery door in the plane.

7. The earcup assembly of claim 1, wherein the battery door covers at least a portion of the second side of the housing when in the second, closed position.

8. The earcup assembly of claim 1, wherein said at least a portion of the second side of the housing comprises at least a portion of the recess.

9. The earcup assembly of claim 1, wherein the battery door covers substantially the entire second side of the housing when in the second, closed position.

10. The earcup assembly of claim 1, wherein at least a portion of the battery door protrudes over at least one edge of the second side of the housing when the battery door is in the second, closed position.

11. The earcup assembly of claim 1, further comprising a loud speaker located inside the housing.

12. A headset comprising the ear cup assembly according to claim 1, further comprising a second earcup assembly.

13. The headset of claim 12, further comprising a headband, wherein at least one earcup assembly is coupled thereto.

14. The headset of claim 13, wherein the second earcup assembly is coupled to the headband via the yoke assembly.

15. The headset of claim 13, wherein the two earcup assemblies are coupled to the headband.

16. The headset of claim 15, wherein the two earcup assemblies are coupled to the headband via respective yoke assemblies.

17. The headset of claim 12, wherein the two earcup assemblies are communicatively or electrically coupled to each other.

18. The headset of claim 12, wherein the ear cup assemblies have the same configuration.

19. The earcup assembly of claim 1, wherein, when the door is in the first, open position, the recess is accessible to a user for inserting/extracting a battery and the battery door is coupled to the housing.

20. The earcup assembly of claim 1, wherein the housing is adapted to lock the battery door in the first position.

* * * * *